United States Patent [19]

Alerasool

[11] Patent Number: 5,345,028
[45] Date of Patent: Sep. 6, 1994

[54] SOLID ACID ALKYLATION USING A SULFATED MIXED OXIDE OF TITANIUM/NICKEL

[75] Inventor: Saeed Alerasool, Huntington, W. Va.

[73] Assignee: Ashland Oil, Inc., Ashland, Ky.

[21] Appl. No.: 28,882

[22] Filed: Mar. 10, 1993

[51] Int. Cl.$^5$ ............................................. C07C 2/58
[52] U.S. Cl. .................................. 585/730; 502/222; 502/337; 502/350; 585/721
[58] Field of Search ................... 585/721, 730, 709; 502/222, 337, 350

[56] References Cited

U.S. PATENT DOCUMENTS

| | | | |
|---|---|---|---|
| 4,384,161 | 5/1983 | Huang et al. | 585/722 |
| 4,918,255 | 4/1990 | Chou et al. | 585/331 |
| 4,956,518 | 9/1990 | Child | 585/726 |
| 4,967,034 | 10/1990 | Miller | 585/446 |
| 5,012,033 | 4/1991 | Child et al. | 585/722 |
| 5,036,035 | 7/1991 | Baba et al. | 502/221 |
| 5,120,897 | 6/1992 | Del Rossi et al. | 585/726 |
| 5,157,199 | 10/1992 | Soled et al. | 585/750 |

FOREIGN PATENT DOCUMENTS 0174836  3/1986  European Pat. Off. .
2071840  3/1990  Japan .

OTHER PUBLICATIONS

"Effect of Acid Strength on the Catalytic Activity of NiO–TiO$_2$ Modified with Acids", by J. R. Sohn, et al., Journal of Catalysis, 127, 449–452 (1991).

"New Solid Acids and Bases", K. Tanabe et al., Studies in Surface Science and Catalysis, vol. 51 pp. 199–213.

Primary Examiner—Asok Pal
Attorney, Agent, or Firm—Richard C. Willson, Jr.; Stanley M. Welsh

[57] ABSTRACT

Disclosed is an alkylation catalyst to form adducts or alkylates of a C$_3$–C$_9$ olefin with a C$_4$ to C$_9$ isoparaffin comprising a sulfated mixed oxide of titanium and nickel, wherein the percent by weight of titanium is at least 80%; of nickel is in the range 1–4%; and of sulfur in the range 1–10%. Also disclosed are the appropriate ratios of olefin to isoparaffin and the use of adamantane to increase yields.

9 Claims, 4 Drawing Sheets

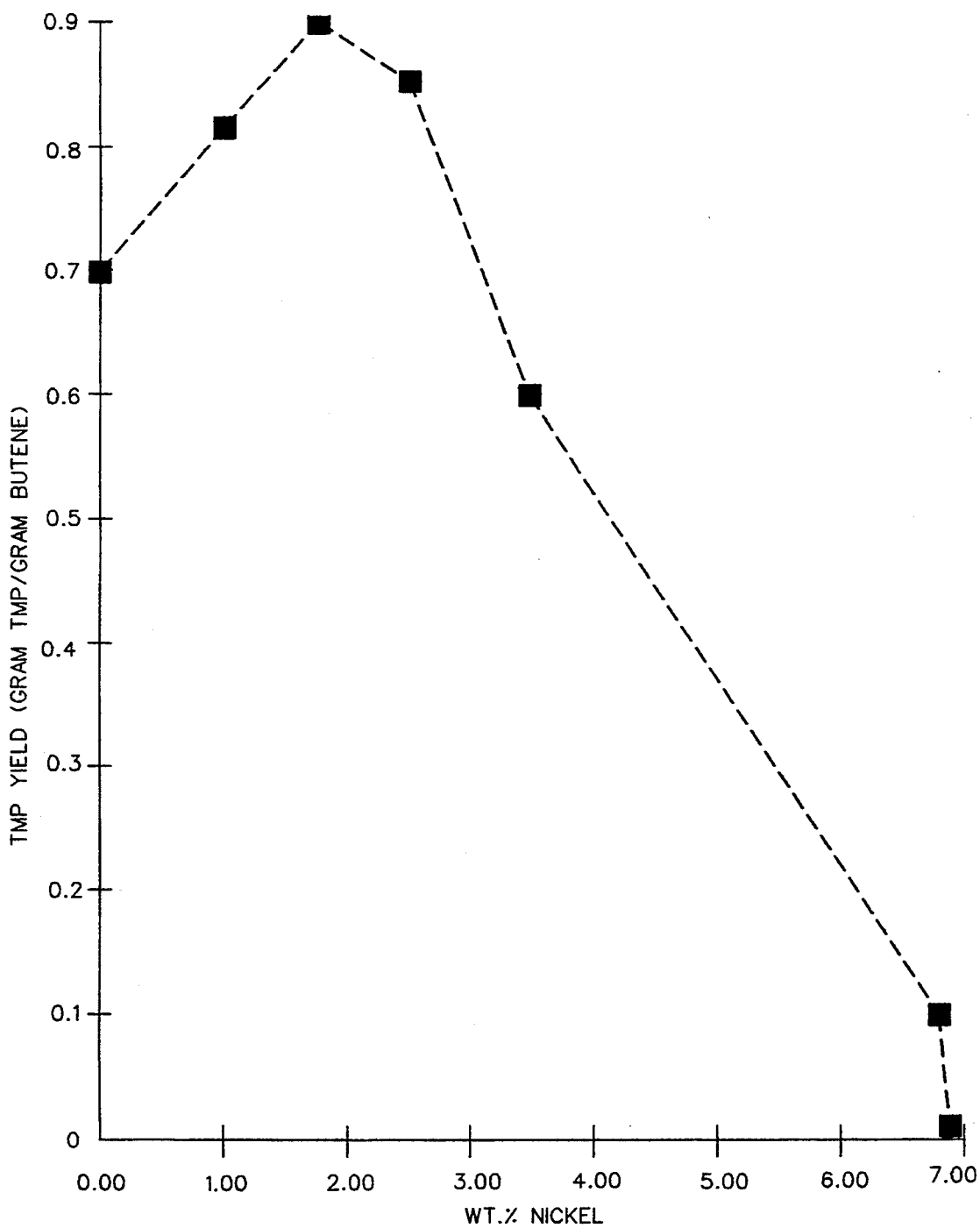

SOLID ACID ALKYLATION USING A SULFATED MIXED OXIDE OF TITANIUM/NICKEL

BACKGROUND OF THE INVENTION

1. Field of the Invention

This invention relates to solid acid catalysts in general. More specifically, this invention is concerned with strong solid acid catalysts suitable to catalyze isoparaffin-olefin alkylation reactions.

2. Description of the Prior Art

A comprehensive text on solid acids and bases was written by Kay Tanabe, et al., entitled *New Solid Acids and Bases Their Catalytic Properties*. In this book there is a section beginning on page 199 entitled *Super Acids*. Discussed in this section were solid acids comprising sulfated oxides of titanium, zirconium, or iron. The use of such compounds is well-known for purposes of acid catalyzed reactions, such as alkylation and cracking. They were found to have higher acid catalyzing properties than sulfuric acid alone. Not discussed or disclosed in this section was the use of mixed oxides; e.g., binary oxides, of super acids to further enhance acid catalyzing properties. No additional metal oxide species in combination with sulfated oxides of titanium, zirconlure, or iron to further enhance their catalytic properties are either disclosed or suggest. A direct comparison of a zirconium oxide promoted with sulfate as contrasted to a titanium oxide promoted with sulfate, with no other factors involved, zirconium uniformly has superior super acid properties.

Alternatively, trying to promote zirconium oxides with additional materials other than sulfate to enhance their acid properties as demonstrated in an example in this case, have uniformly been found not to yield superior acidic properties. In other words, a nickel oxide zirconium mixed oxide matrix promoted by sulfate does not lead to an enhanced solid acid having properties superior to the zirconium oxide without the nickel promotion. In an example of this Specification, mixed nickel and zirconlure oxide matrices having nickel in concentration range 0.1 to 3.3 wt % were tried and promoted with sulfate concentrations in the range 2.0 to 4.2 wt %. The results are reported in a table and an associated graph.

Other methods of promoting solid acidity that appear in the literature have to do with the addition of a platinum metal to a super acid oxide. The platinum apparently is not an oxide, but is functioning like a hydrogenation transfer agent. Platinum is known to cause the homolytic scission of hydrogen to hydrogen bonds. Its presence in a strong solid acid has been hypothesized to encourage ionic scission of hydrogen to hydrogen bonds, i.e. to form H+ and H−type species. There is nothing in the promotion of solid oxides by the presence of platinum that suggests that the platinum is in the form of an oxide or functions through an oxide structure. Some improvement has been reported as a result of the addition of platinum as a platinum metal. This is to be distinguished from the advantages disclosed in the instant invention for an oxide of a Group VIII metal.

In an article entitled *Effect of Acid Strength on the Catalytic Activity of NiO-TiO$_2$ Modified with Acids* of J.R. Sohn, et al., published in JOURNAL OF CATALYSIS, 127, 449-452 (1991), the co-precipitation of nickel hydroxide and titanium hydroxide by adding ammonium hydroxide slowly to a mixed solution of nickel chloride, titanium chloride, and hydrochloric acid at room temperature produced a precipitated material, which after thorough washing to remove chloride, was dried at room temperature for 12 hours. Other methods of drying the chloride-free precipitate, indicate an evacuated chamber at a temperature of 400° C. for 1.5 hours in contrast to the 12 hours. The catalyst was used for purposes of isomerization of 1-butene. No other catalytic reactions were suggested or disclosed. A nickel oxide content was reported to be 25 mole % in the only example showing the isomerization properties of the catalyst. Mention of a catalyst being prepared having a nickel oxide content of 4 mole % was also made. However, the 4 mole % was used to keep the content of nickel down so that Hammett Indicators could be used. Hammett Indicators give rise as was explained in the article to color changes dependent upon the acid strength of the catalyst. However, if the catalyst itself were colored, this tended to mask any color changes that would otherwise be observable by means of Haminert Indicators. Consequently, the low concentration of nickel oxide was not due to any attempt to maximize or explore lower concentrations of nickel for purposes of catalyzing isomerization reactions but rather only to be able to better determine color changes of certain Hammett Indicators.

The instant invention distinguishes over the materials disclosed in this *Journal of Catalysis* article because the nickel content of their isomerization catalyst was far outside of any range suitable for the instant invention. In fact, it has been found that increasing weight percent or mole percent of nickel leads to a progressive decrease in alkylation activity. Not disclosed in this article is the criticality of nickel oxide content nor the use of the catalyst for purposes other than isomerization.

In U.S. Pat. No. 5,036,035 (issued Jul. 30, 1991) entitled *Solid, Strong Acid Catalyst Process for the Production of the Same and Use Thereof*, a solid strong acid catalyst useful for hydrocarbon reactions, specifically skeletal isomerization, is disclosed wherein supported sulfate ions in the presence of Group III, Group IV, and Group VIII metals are disclosed. The Group VIII metals include nickel, platinum, ruthenium, rhodium, palladium, osmium, and uranium. The Group III metals include aluminum, gallium, indium, and thallium. The Group IV metals include titanium, zirconium, silicon, germanlure, and tin. Longer catalyst life of the sulfated oxide was discovered to result from the presence of Group VIII metals and sulfate. Essentially, a Group VIII metal was added to a support of hydroxides or oxides of Group IV and/or Group III metals. The only instance of co-precipitation disclosed anywhere in the specification consisted of the preparation of a Group III and Group IV metals together to form the support. In no instance is there an example of the co-precipitation of titanium, a Group IV metal, and nickel, a Group VIII metal. The incorporation of a Group VIII metal was disclosed to be either before, after, or simultaneous with sulfation. There is reported to be a benefit from first sulfating by treating with a metal-free sulfate-containing agent and then introducing the Group VIII metals thereon. Also reported is the fact that it is important to effect calcining and stabilizing treatment at a temperature of 450° to 800° C. Lower temperatures are suggested as possible, but not preferred. Perhaps the higher temperature calcination is preferred in the case of sequential precipitation in contrast to the instant invention that prefers temperatures of calcination not exceeding 450° C. for a mixed oxide. A mixed oxide is a unique material that results, from co-precipitated hydroxides of nickel and titanium. Not disclosed are the dual limitations of nickel oxide content, which is not significantly higher than 4% by weight, and a calcination temperature not exceeding 450° C. In summary, there is no teaching in which a Group VIII and a Group IV or Group III oxide or hydroxide are co-precipitated to form a solid which is subsequently sulfated, nor is the content of nickel or the calcination temperature taught to be critical.

For a comprehensive background in alkylation reactions that are relevant to this invention, see *Industrial and Laboratory Alkylations,* vol. 55 (1977) of the American Chemical Society Symposium Series, edited by L.S. Albright and A.R. Goldsby. Other references of relevance are: U.S. Pat. No. 5,120,897 to Del Rossi, et al. (Jun. 09, 1992); U.S. Pat. No. 4,956,518 to Child et al. (Sep. 11, 1990); U.S. Pat. No. 4,967,034 to Miller et al. (Oct. 30, 1990); U.S. Pat. No. 4,918,255 to Chou et al. (Apr. 17, 1990); U.S. Pat. No. 5,012,033 to Child et al. (Apr. 30, 1991); and U.S. Pat. No. 4,384,161 to Huang et al. (May 17, 1983). Adamantane has been disclosed in U.S. Pat. No. 5,157,199 to Soled et al. (Oct. 20, 1992) to catalyze isomerization.

SUMMARY OF THE INVENTION

1. General Statement of the Invention

Broadly, this invention is directed to the formation of a mixed oxide of titanium and nickel. It has been discovered that a surprising degree of acidity can be achieved by formation of a mixed oxide followed by deposition of sulfate groups.

Art directed to the use of highly acidic super acids containing titanium and nickel for alkylation reactions, do as not disclose nor involve the interaction between the titanium and nickel resulting from a mixed oxide. A mixed oxide for purposes of this specification and claims means a mixture of two or more metal oxides which are "chemically" combined in a primarily amorphous structure. "Chemically" means in this context that there is a common sharing of some oxygens of titanium oxides present with nickel, i.e. a Ni-O-Ti structural unit. Mixed oxides can occur as a result of co-precipitation, but never as a result of impregnation or sequential precipitation of one metal oxide onto or into another. Impregnation and sequential deposition are established in an example of this specification not to result in a titanium/nickel mixed oxides.

Art that has involved the acid strength of nickel/titanium mixed oxides have been directed to catalyzing reactions other than alkylation reactions. Specifically the closest reference found was discussed in this specification. It did not disclose the criticality of the nickel oxide content on a mixed oxide catalyst's ability to catalyze alkylation reactions.

It is an object of this invention to provide a catalyst suitable for alkylation reactions, e.g., isoparaffin additions to olefins, that enhances the catalytic effectiveness of sulfated titanium oxide catalysts to effect such alkylation reactions. Alkylation reactions are primarily intended to cover the contacting of $C_3$–$C_9$ mono-olefins with $C_4$–$C_9$ isoparaffins at suitable reaction conditions in the presence of the catalyst of this invention to produce adducts.

It was surprising to us to find that nickel enhanced the sulfated titanium oxide catalyzing properties for alkylation, even though prior attempts to enhance alkylation catalyzing properties for sulfated zirconium oxide through nickel co-precipitation catalysts showed no improvement over zirconium oxide catalysts alone and even a reduced ability at times to catalyze alkylation reactions between, for example, isobutane and n-butene.

We have discovered that the mixed oxide suitable to this invention must be prepared in such a way that there is a large excess of titanium over the nickel. Specifically, the precipitation of the nickel cannot occur subsequent to the formation of the titanium matrix. For example, if one begins with a titanium support, one cannot by means of ion exchange or subsequent precipitation form a mixed oxide catalyst having the properties of the instantly disclosed and claimed invention.

Preferably a catalyst of this invention comprises the following composition: At least 80%, and preferably 90% by weight titanium; 1 to 4%, and preferably 2 to 4% by weight nickel; and 1 to 10%, and preferably 2 to 5% by weight sulfur, wherein there is a mixed oxide structure of Ti and Ni oxides, i.e. a Ti-O-Ni structural unit present.

The precise or minimum amount of titanium that must be present is determined by the fact that co-precipitation of titanium hydroxide and nickel hydroxide onto the catalyst is such that the nickel finds itself in an environment dictated by the titanium oxide matrix. In Kay Tanabe, et al.'s book entitled *New Solid Acids and Bases Their Catalytic Properties,* co-precipitation of silica and titania is described to form a mixed oxide, in which the species which is in excess determines the oxide environment for the other species. Tanabe, et al. discussed co-precipitation with an excess of silica over titania and vice versa. In summary, there must be a large excess of titania over nickel to ensure that the mixed oxide has an oxide environment dictated by the titanium.

Preferably, the process of alkylation of this involves in the presence of catalysts of this invention contacting one or more mono olefins, having from 3 to 9 carbon atoms with an isoparaffin having from 4 to 9 carbon atoms at a temperature and pressure sufficient to produce primarily adducts. Generally a temperature in the range- 40° C. to about 450° C., preferably −30° C. to about 400° C., and most preferably 0° C. to about 350° C. are suitable. Generally a pressure in the range of 10 psig to about 5000 psig, preferably 14 psig to about 3500 psig, most preferably 20 psig to about 3000 psig are suitable. Generally, the hydrocarbon feed comprising an olefin and isoparaffin, has an average molar ratio of the isoparaffin: olefin in the range of about 1:1 to 1000:1, preferably 1:1 to 500:1, more preferably 1:1 to 50:1, and ideally 1:1 to 10:1.

2. Utility of the Invention

The essential benefits provided by the solid acid catalysts of this invention are:

1. High acid strength at least as useful as that obtainable from hydrofluoric acid or sulfuric acid for isoparaffin alkylation reactions; and 2. An environmentally acceptable catalyst that overcomes the difficulties and environmental hazards associated with hydrofluoric acid or sulfuric acid;

Acid density means the number of acid sites per gram as determined thermogravimetricly by analyzing the amount of pyridine adsorbed at 150° C. The precise analytical technique followed for determining acid density is given in an example to this Specification.

In order to achieve the benefits of this invention for purposes of alkylation reactions, e.g. the reaction of isobutane with an alkene, we have discovered that a co-precipitation to form a mixed oxide is required wherein the predominant specie determining the oxide environment of the nickel is titanium. We have found for example that where zirconium is the predominant specie determining the oxide environment of the nickel, the enhancement properties of the super oxide resulting as a result of sulfation does not occur in the case of zirconlure but was found, surprisingly, to occur in the case of titanium. We have also found that in addition to forming the mixed oxide, one must keep the content of nickel and sulfur significantly low, and the content of titanium at least 50% by weight and higher, preferably at least 75%, and most preferably at least 85%. In the case of nickel, not much in excess of 4, generally in the range of 1 to 4 weight percent and preferably 2 to 4 weight percent for nickel. In the case of sulfur, the sulfur content must not significantly exceed 10% by weight and generally such content is in the range 1 to 10% by weight, preferably in the range of 2 to 5% by weight. We have found that excess sulfur has a detrimental effect on alkylation reactions. We have also found that increasing amounts of nickel tends to decrease alkylation activity. This is intriguing in so far as there is an apparent increase in acid density with increasing amounts of nickel but instead of increasing activity, apparently there is a decreasing activity with respect to alkylation reactions.

3. Disclosed in summary are such critical limitations as the formation and maintenance of a "mixed oxide" of titanium and nickel, the proper content of sulfur and nickel, and heat treatments such as calcinations of the catalyst which must not exceed 450° C., that permit high acid densities that cause a higher yield per gram of catalyst not otherwise available from most solid acid catalysts are obtained.

BRIEF DESCRIPTION OF THE DRAWINGS

FIG. 4 discloses the effect of calcination temperature in conjunction with the three methods of preparation considered in FIG. 2.

EXAMPLE I

Figure 1:
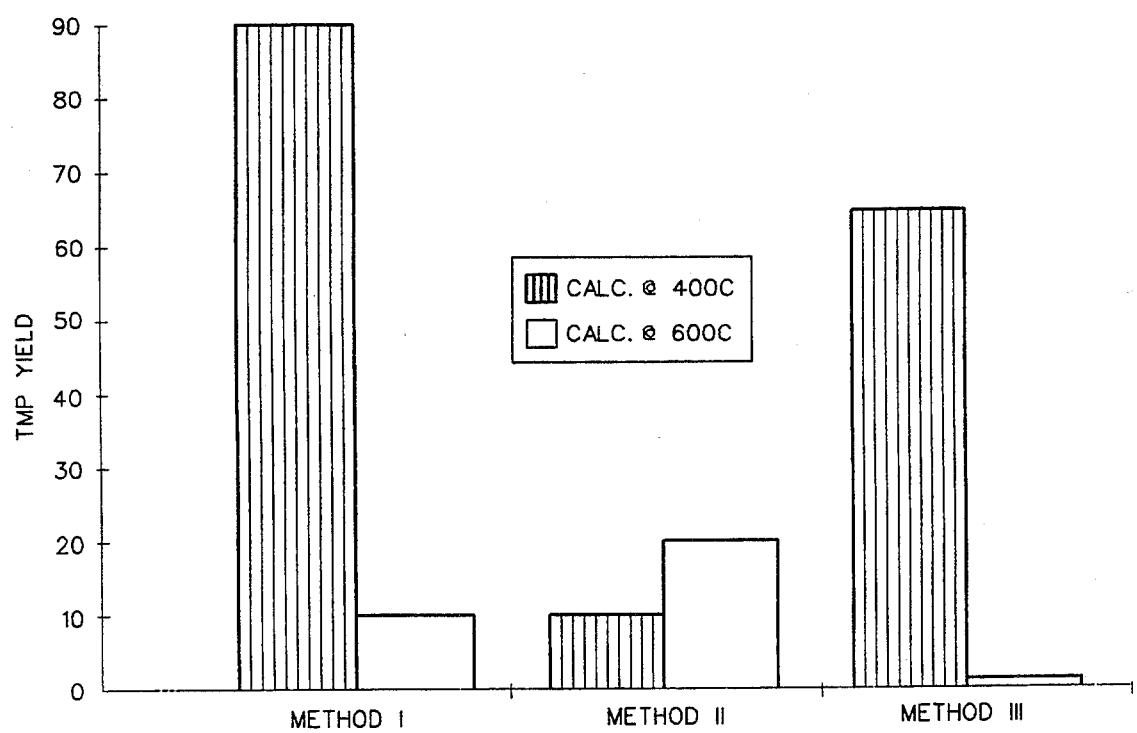
FIG. 1 is a graph disclosing the yield of trimethylpentane ("TMP") on a gram of trimethylpentane per gram of butane added as a function of weight percent nickel in the titanium nickel mixed oxide catalyst made in accordance with Method 1. Method 1 is discussed in Example 2.

Acid densities for catalysts of this invention are determined thermogravimetrically by adsorption, and desorption of adsorbed pyridine. The steps for determining the irreversible adsorption of pyridine are as follows:

In a thermogravimetric apparatus, the weight of the catalyst is followed as a function of time and calcination temperature of 400° C. When the lowest weight is determined and maintained, the catalyst is cooled to 150° C., during which time a mixture of pyridine and nitrogen is introduced into the apparatus. There follows an increase in weight over time of the sample at 150° C. When the maximum weight is observed and stabilized, pyridine is removed from the stream and a stream of substantially pure nitrogen is used. The weight of the sample at constant temperature of 150° is followed until a final weight is observed. Acid density is equal to ($10^6$/molecular wt. % of pyridine) times the ratio of the final weight $W_f$, minus initial weight $W_i$, divided by the initial weight. Acid density is in units of micro moles of pyridine per gram of catalyst, and has the formula:

$$\{(W_f-W_i)/(W_i \times 79)\} \times 10^6 = \text{Acid Density}$$

Usually one gets an excellent correlation between normalized hexane cracking activity and trimethylpentane (TMP) yield. To normalize the activity of all catalysts, the ratio of total acid sites to number of olefin molecules in each charge to the reactor as maintained constant by adjusting the weight of catalyst used in the reactor.

However, surprisingly, with respect to the instant invention, this correlation does not work, since hexane cracking was found unsatisfactory due to the catalyst rapidly deactivating.

Table 1 below correlates acid densities with other process parameters of preparation and sulfur content.

| Catalyst | I.D. | Preparation Method | Calcination Temp. (°C.) | Wt. % S | Wt. % Ni | Surface Area (m²/g) | Acid Density μmole/g |
|---|---|---|---|---|---|---|---|
| SO4/TiO2 | AL0621-B | I | 400 | 02.33 | 0.00 | 90 | 207 |
| SO4/ZrO2 | AL0379-1A | I | 400 | 4.00 | 0.00 | 180 | 328 |
| S/NiZr | AL0760 | I | 400 | 4.80 | 1.00 | 162 | 370 |
| S/NiTi | AL0610 | I | 400 | 3.35 | 3.50 | 142 | 479 |
| S/NiTi | AL0610-D | I | 400 | 3.00 | 1.60 | 131 | 355 |
| S/NiTi | AL0610-A | I | 400 | 5.48 | 2.59 | 93 | 227 |
| S/NiTi | AL0610-E | I | 400 | 3.13 | 4.60 | 134 | 362 |
| S/NiTi | AL6010-C | I | 400 | 3.25 | 6.80 | 152 | 460 |
| S/NiTi | AL0610-B | I | 400 | 2.88 | 6.87 | 160 | 506 |
| S/NiTi | AL0611-A | I | 600 | 1.76 | 2.58 | 41 | 152 |
| S/NiTi | AL0610-I | II | 400 | 2.8 | 2.9 | 161 | 362 |
| S/NiTi | AL0610-J | III | 400 | 2.60 | 3.00 | 51 | 130 |
| S/NiTi | AL0611-C | III | 600 | 1.5 | 2.9 | 7 | 34 |
| S/NiTi | AL0611-D | II | 600 | 1.5 | 3.4 | 69 | 168 |

Method I: Prepared by Co-Precipitation (Method of this Invention)
Method II: Prepared by Impregnation of Ti(OH)4 with Ni
Method III: Prepared by Impregnation of TiO2 with Ni
*Kirsch et al. U.S. Pat. No. 3,865,894

EXAMPLE II

Catalyst Preparation And Testing

The catalyst of the present invention was prepared according to a method referred to herein as Method I. In order to demonstrate the superior properties obtained by Method I, for the purpose of isoparaffin/olefin alkylation, catalysts of comparable compositions were prepared by two alternate methods referred to herein as Methods II and III. To determine the effects of calcination temperature on the catalyst properties and performance, calcination temperatures of 400° C. and 600° C. were used for final treatment of the catalyst samples. Catalysts designated by AL0610 were all calcined at 400° C. while the AL0611 series were calcined at 600° C. The detailed description of the three preparation methods are as follows:

Method I. A calculated amount of $NiCl_2.6H_2O$ (ranging between 8 to 24 grams) was dissolved in a beaker containing between 30 to 35 ml of $TiCl_4$, 200 cc of deionized water, and 50 ml of hydrochloric acid. The precise amount of $NiCl_2.6H_2O$ was calculated based on the final desired nickel content which varied between 1 and 7 percent by weight. The pH of the resulting solution was adjusted to 7.0–7.5 by the dropwise addition of $NH_4OH$. A precipitate was formed upon increasing the pH. This precipitate was washed with approximately 2 to 3 liters of deionized water and was dried in a vacuum oven at 120° C. The dried sample was treated with 2 N sulfuric acid. This was accomplished by placing catalyst over a filter paper and pouring acid on it. The amount of sulfuric acid solution used for the sulfating acid ranged between 20 to 35 cc per gram of catalyst to achieve sulfur contents ranging between 3 to 5 percent by weight. Following the drying step, the catalyst was dried for 12 hours at 120° C. The dried catalyst was calcined in air at 400° C. for 12 hours. The six catalysts prepared by this method with their nickel contents ranging between 1.6 and 7.3 weight percent were labeled AL0610 and AL0610-A through AL0610-E. The composition, surface area, and acidity of these catalysts are listed in Table I. The concentration of nickel in the solid samples were determined by x-ray fluorescence spectroscopy (XRF). To investigate the effect of calcination temperature, a portion of AL0610-A was also calcined at 600° C. and was labeled AL0611-A.

Method II. Dissolved 100 ml of $TiCl_4$ in a solution obtained by diluting 100 ml of concentrated HCl with 400 ml of deionized water. Neutralized the resultant solution with ammonium hydroxide to a pH of 7.0. Filtered and washed the resultant $Ti(OH)_4$ precipitate with deionized water until no chloride ions were detected in the filtrate. Upon washing $Ti(OH)_4$ and removing all chloride ions, it was dried in a vacuum oven at 120° C. for twelve hours. Twenty-one grams of the dried $Ti(OH)_4$ species were slurried in approximately 25 cc of deionized water 2.7 g of $Ni(NO_3)_2.6H_2O$ was added to this slurry and stirred. After it was assured that all of the $NiCl_2.6H_2O$ species had been dissolved, the mixture was left in a vacuum oven at 120° C. for another twelve hours until a dry solid was obtained. Half of the dried catalyst was calcined in air for 12 hours at 400° C. and labeled ALO610-I while the other half was calcined at 600° C. and labeled AL0611-D.

Method III. About twenty five gram of the $Ti(OH)_4$ prepared above was calcined in air at 400° C. for twelve hours. High temperature calcination led to the formation of twenty-two grams of $TiO_2$. A solution consisting of 3.4 grams of $Ni(NO_3)_2.6H_2O$ and about 5 cc of deionized o water was slowly added to the $TiO_2$ sample. The mixture was vigorously stirred for approximately thirty minutes and was then placed in a vacuum oven over night. The dried sample was calcined at 400° C. for twelve hours and was labeled ALO610-J. The same preparation was repeated with another twenty-five gram sample of $Ti(OH)_4$ except that the impregnated sample was calcined at 600° C. This sample was labeled ALO611-C.

Procedure for Testing Alkylation Performance of Each Catalyst

An amount of catalyst ranging between 2 to 11 grams was placed a 300-ml stainless steel autoclave reactor. The catalyst was activated by flowing dry nitrogen at 360° C. for three hours through the autoclave reactor. The reactor was then cooled to room temperature and was charged with 180 ml of isobutane. This was followed by heating to 93° C. and pressurizing the autoclave to 300 psig to assure that all of the isobutane is in liquid phase. A series of eight 0.14-ml pulses of 1-butene was then sent to the reactor. The time between each pulse was approximately twenty minutes. The content of the reactor was transferred to a stainless steel cylinder and was submitted for detailed hydrocarbon analysis by capillary GC. The primary quantity used for evaluating and ranking catalysts was the yield of trimethylpentane (also referred to as TMP yield). Trimethylpentane was used as the product of choice since it has the highest octane value—unlike dimethylhexane (DMH) and other $C_8$ products. The TMP yield is defined as the total amount of TMP formed divided by the total mass of 1-butene charged to the reactor. Other quantities of interest were the $C_5+$ yield which is defined as the total amount of hydrocarbons larger than or equal to $C_5$ per gram of olefin charged. In order to insure that all catalysts were evaluated under the same conditions the amount of catalyst used in every experiment was adjusted such that the ratio of total number of acid sites of the catalyst to the molecules of olefin charged in each pulse was maintained between 0.5 and 1.5. Therefore, larger quantities of catalysts with substantially lower acid densities were used in order to compensate for their low acid density. The results of all performance tests are summarized in Table II.

EXAMPLE III

Effect of Different Calcination Temperatures on Trimethylpentane Yields

FIG. 1 discloses the effect of calcination temperatures on the three different methods of preparation discussed in Example II. It was found that if one calcined at 400° C., the activity of the catalyst was maintained. But if one calcined at 600° C., there was a dramatic decrease in catalytic activity. This was especially true of Methods 1 and 3. With respect to Method 2, the activity of the catalyst was so low, any differences between the two calcination temperatures of 400° and 600° C. were within experimental error.

It was found that the crystalline structure of the different catalyst dramatically changed as a result of differences in calcination temperature. The mixed oxide of the instant invention tends to be amorphous. Whereas at higher temperatures the phases tend to form discrete crystallites phases. It is believed that during crystallite formation, the amorphoric mixed oxide structure is lost. Note that merely because one has an amorphous phase after a 400° C. calcination, does not ensure the presence of a mixed oxide. This is clear because in Methods 2 and 3 the 400° calcination led to an amorphous phase which later became crystallite or more crystallite at calcination temperatures of 600° C. Of importance is that the trimethylpentane (TMP) yield from Method 1 is at least 20% higher than that yield of trimethylpentane obtained by a catalyst prepared in accordance with Method 3, assuming both had been calcined at 400° C. This example demonstrates the criticality of calcining, not significantly in excess of approximately 450° C.

EXAMPLE IV

Effect of Preparation Method on Alkylation Performance of the Catalyst

Figure 2:
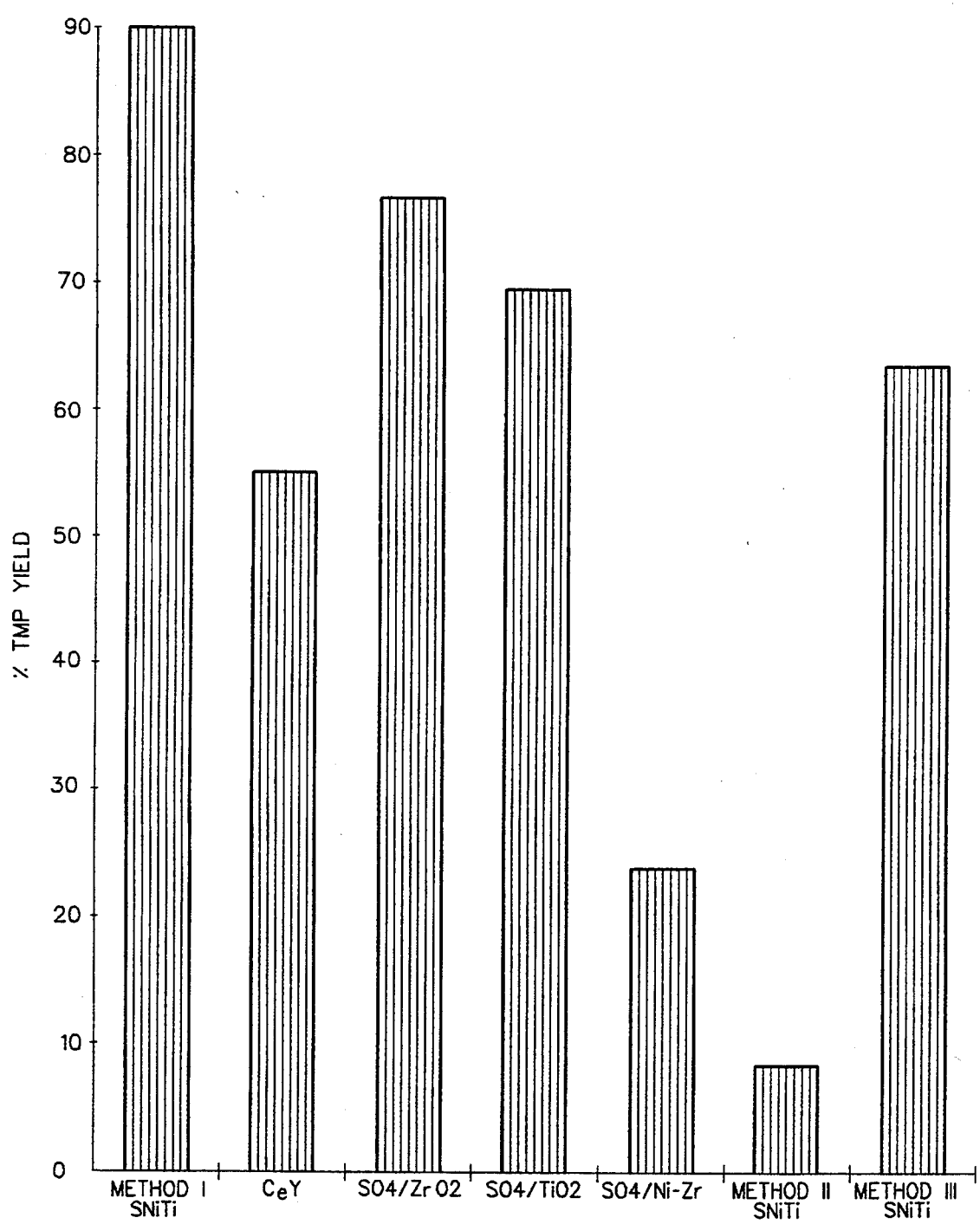
FIG. 2 and FIG. 3 disclose the consequences of the three different methods of catalyst preparation discussed in Example 2 upon percent TMP yield and TMP to DMH ("dimethylhexane") ratios, respectively.
Figure 3:
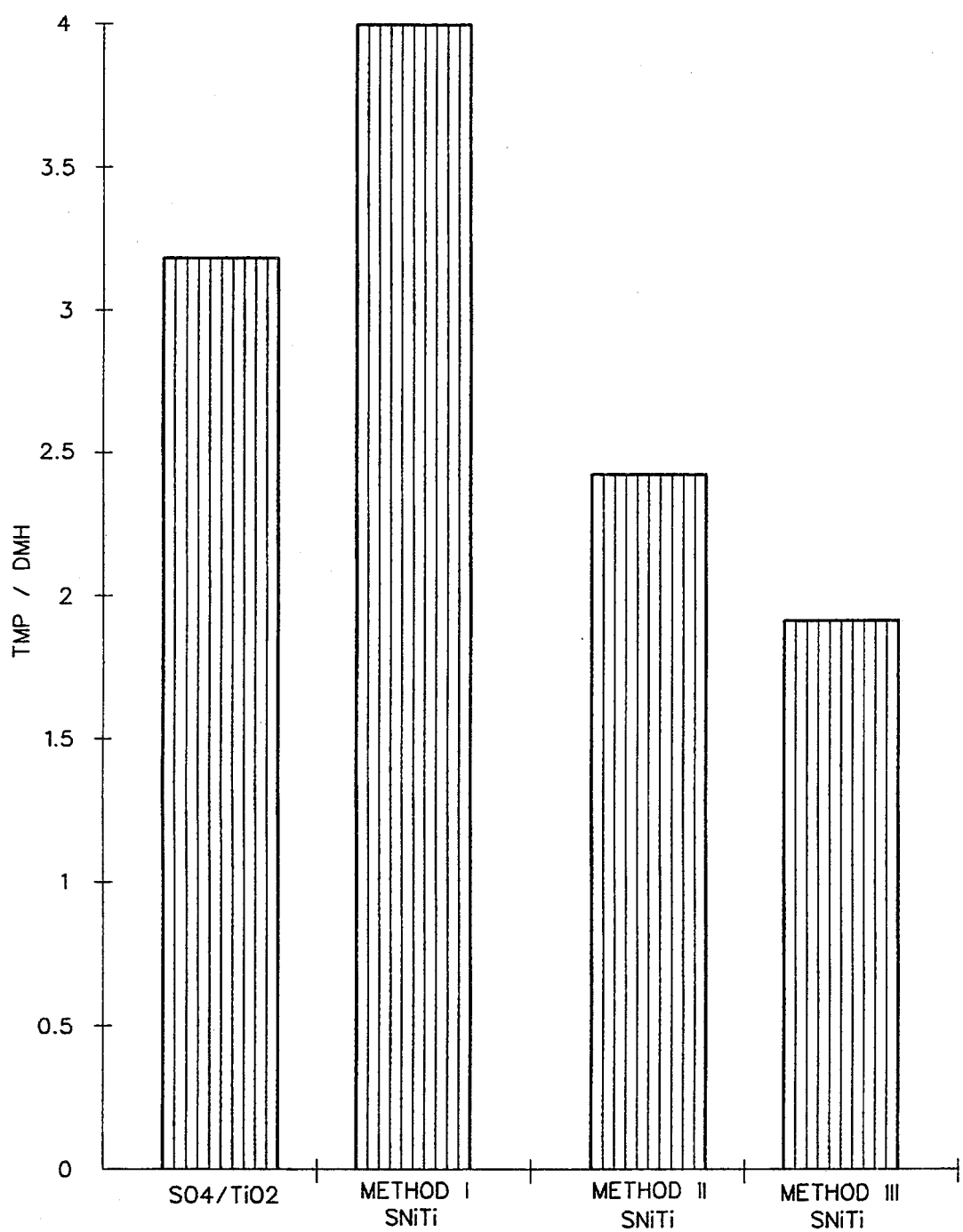

FIGS. 2 and 3 disclose the alkylation performance of catalysts prepared with Methods 1, 2, and 3. To establish a benchmark for these catalyst, the catalyst in accordance with Kirsch, et al., U.S. Pat. No. 3,865,894 and sulfated titanium oxide are also included.

From FIG. 1, it is clear that Method 1 is superior to Methods 2 and 3, and also superior to either a simple sulfated titanium or a catalyst prepared in accordance with U.S. Pat. No. 3,865,894.

FIG. 1 discloses a result that is especially surprising in view of the fact that nickel promotes a sulfated titanium, whereas nickel did not promote a sulfated zirconium. It is to be recalled that sulfated zirconium tended to be a higher and more active alkylation catalyst than a sulfated titanium oxide.

FIG. 2 shows also an additional interesting result and benefit that is achieved by applying Method 1 to a sulfated nickel titanium mixed oxide catalyst in the ratio of trimethylpentane to dimethylhexane that is produced. The ratio of trimethylpentane to dimethylhexane is highest in the case of Method 1 preparation for a sulfated nickel titanium mixed oxide. This benefit is important because to maximize octane values of alkylation products, as much excess trimethylpentane over dimethylhexane as possible is desired; the octane value of trimethylpentane is much higher than that of dimethylhexane.

EXAMPLE V

Effect of Nickel Content on Optimum Preparation at Optimum Calcination Temperatures FIG. 4 discloses the alkylation activity of a catalyst made with the optimum method, Method 1, that has been calcined at 400° C. with the only variable being the weight percent nickel. The trimethylpentane yield is in grams of TMP per gram of butane added in accordance with the reaction procedures discussed in Example 2.

From FIG. 4, it is clear that as the weight percent nickel increases, initially there is an increase in trimethylpentane yield to a maximum at a weight percent of nickel around 3. As one increases the weight percent nickel beyond 3, the trimethylpentane yield dramatically drops off. In point of fact, the effectiveness of the nickel content is totally lost over the sulfonated titanate oxide catalyst without nickel at a concentration around 4 weight percent nickel.

It is interesting to note that the acid density was found to increase with increasing nickel content throughout the range of 0 to 7 shown in the FIG. 4. In other words, as one increases the nickel content much beyond 3 wt. %, even though one is still increasing the acid density, alkylation performance drops off.

EXAMPLE VI

Comparative Examples

Table 2 below discloses the various sulfate and titanium catalyst prepared in light of a baseline established by Kirsch et al. in U.S. Pat. No. 3,865,894 and a sulfated titania catalyst. Catalyst preparation Method 1 corresponds to a co-precipitation leading to a mixed oxide. Catalyst Method 2 is a sequential precipitation of titanium hydroxide and nickel hydroxide without a calcination step between the deposition of titanium hydroxide and nickel hydroxide. Method 3 is an impregnation of nickel hydroxide onto a titanium hydroxide followed by a calcination. For details of these methods, see Example 2. All reactions were run at 93° C. with the exception of the baseline Kirsch case which was run at 120° C. All reactions were run in accordance with the method discussed in Example 2. From the table, it is clear that sulfated zirconlure oxide is better than sulfated nickel zirconlure co-precipitated in accordance with Method 1. The table also shows that a sulfated zirconlure oxide tends to be a superior catalyst to a sulfated titanium oxide catalyst. Both made in accordance with Method 1 discussed in Example 2.

The performance of each catalyst was determined with respect to TMP yield percent, where TMP yield percent is the ratio of all TMP formed divided by total olefin charged to the reactor summarizing all pulses of olefin that have been added. The yield is a cumulative number that resulted from all additions of olefin rather than each incremental addition.

TABLE 2

Product Distribution of Various SO4/Ni—Ti Catalysts

| Catalyst | CeY | SO4/Ni—Ti | SO4/Ni—Ti | SO4/Ni—Ti | SO4/Ni—Ti | SO4/Ni/Ti | SO4/Ni—Ti | SO4Ni/Ti |
|---|---|---|---|---|---|---|---|---|
| Catalyst Prep Method | * | I | I | I | I | I | II | III |
| Catalyst postreatment Temp (°C.) | 400 | 400 | 400 | 400 | 400 | 400 | 400 | 400 |
| Catalyst ID | N/A | AL0610 | AL0610-A | AL0610-B | AL0610-D | AL0610-E | AL0610-I | AL0610-J |
| Run # | 738° | B2023-003 | B2023-040 | B2023-017 | B2023-041 | B2023-063 | B2023-168 | B2023-170 |
| wt % Ni | N/A | 3.5 | 3 | 7.37 | 1.6 | 4.6 | 2.9 | 3 |
| Wt % S | N/A | 3.4 | 5 | 2.83 | 3 | 3.1 | 2.8 | 2.6 |
| Reaction Temperature (°C.) | 120 | 93 | 93 | 93 | 93 | 93 | 93 | 93 |
| Catalyst Weight (g) | — | 3 | 6.6 | 3 | 4.3 | 4.2 | 4.1 | 10.7 |
| TMP Yield % | 55 | 85 | 90 | 0 | 83 | 61 | 9 | 66 |
| C5 + Paraffin Yield % | 129.4 | 119 | 123 | 9 | 113 | 102 | 7.2 | 125 |
| C5 + Paraffin Distribution (mole %) | | | | | | | | |
| C9+ | 10.7 | 1.5 | 0 | 37.5 | 0 | 1.9 | 8.3 | 0 |
| C8 | 54.7 | 80.5 | 88.8 | 62.5 | 92.8 | 77 | 68.1 | 79.6 |
| C7 | 12 | 7.2 | 3.4 | 0 | 4 | 5.5 | 4.2 | 5.6 |
| C6 | 8.9 | 4.2 | 2.7 | 0 | 3.2 | 5.8 | 5.6 | 5.4 |
| C5 | 13.7 | 6.7 | 5 | 0 | 0 | 9.7 | 13.9 | 9.4 |

TABLE 2-continued

Product Distribution of Various SO4/Ni—Ti Catalysts

| C8 Paraffin Distribution, mole % | | | | | | | | |
|---|---|---|---|---|---|---|---|---|
| TMP | 74 | 85.6 | 78.2* | 0 | 79.5 | 74.2 | 63.3 | 61.9 |
| DMHx | 24.6 | 12.9 | 19.7 | 0 | 19.1 | 23.6 | 26.5 | 33 |
| MHp | 1.5 | 0 | 0 | 0 | 0 | 0 | 0 | 0 |
| TMP/DMHx | 3.0 | 6.6 | 4.0 | 0.0 | 4.2 | 3.1 | 2.4 | 1.9 |
| Unknown | 0 | 1.5 | 2.1 | 0 | 1.4 | 2.2 | 10.2 | 5.1 |
| TMP Distribution | | | | | | | | |
| 2,2,4 | 31.5 | 48.5 | 57 | 0 | 52.1 | 48 | 29 | 61 |
| 2,2,3 | 6.4 | 2.5 | 5.3 | 0 | 2.9 | 2.4 | 9.7 | 5.9 |
| 2,3,4 | 31.3 | 28.4 | 18.5 | 0 | 28.4 | 34.4 | 41.9 | 15.9 |
| 2,3,3 | 30.8 | 20.6 | 19.2 | 0 | 16.6 | 15.2 | 19.4 | 17.2 |

| Catalyst | SO4/Ni—Ti | SNi/TiO2 | SNi/TiO2 | SO4/TiO2 | SO4/Ni—Zr | SO4/ZrO2 |
|---|---|---|---|---|---|---|
| Catalyst Prep Method | I | III | II | — | I | — |
| Catalyst postreatment Temp (°C.) | 600 | 600 | 600 | 400 | 400 | 400 |
| Catalyst ID | AL0611-A | AL0611-C | AL0611-D | AL0621-B | AL0760 | AL0379-1A |
| Run # | B2023-004 | B2023-174 | B2023-171 | B2023-064 | B2023-089 | B2023-012 |
| wt % Ni | 2.58 | 3 | 2.9 | 0 | 1 | 0 |
| Wt % S | 1.76 | 2.6 | 2.8 | 2.4 | 4.8 | 4 |
| Reaction Temperature (°C.) | 93 | 93 | 93 | 93 | 93 | 93 |
| Catalyst Weight (g) | 6 | 0 | 4 | 7.2 | 4.6 | 3 |
| TMP Yield % | 9 | 0 | 19 | 73 | 25 | 77 |
| C5 + Paraffin Yield % | 51 | 0 | 13 | 125 | 85 | 118 |
| C5 + Paraffin Distribution (mole %) | | | | | | |
| C9+ | 8.2 | 0 | 2.2 | 2.1 | 0 | 1 |
| C8 | 68.9 | 0 | 71.3 | 72 | 82.3 | 86.6 |
| C7 | 4.9 | 0 | 5.9 | 7.9 | 4.3 | 3.7 |
| C6 | 4.9 | 0 | 5.1 | 7.9 | 4.3 | 2.9 |
| C5 | 13.1 | 0 | 15.4 | 10.1 | 9.1 | 5.9 |
| C8 Parafffin Distribution, mole % | | | | | | |
| TMP | 73.6 | 0 | 64.3 | 75.3 | 68.3 | 73.7 |
| DMHx | 19.2 | 0 | 27.5 | 23.9 | 27 | 23.8 |
| MHp | 0 | 0 | 0 | 0 | 0 | 0 |
| TMP/DMHx | 3.8 | 0 | 2.3 | 3.2 | 2.5 | 3.1 |
| Unknown | 7.2 | 0 | 8.2 | 0.9 | 4.7 | 2.5 |
| TMP Distribution | | | | | | |
| 2,2,4 | 32.3 | 0 | 48.1 | 47.2 | 49.8 | 52.1 |
| 2,2,3 | 9.7 | 0 | 4.8 | 3.3 | 4.6 | 3.8 |
| 2,3,4 | 35.6 | 0 | 33.7 | 30.9 | 29.1 | 26.1 |
| 2,3,3 | 22.4 | 0 | 13.4 | 18.6 | 16.4 | 17.9 |

*Kirsch et. al, U.S. Pat. No. 3,865,894

Modifications

Specific compositions, methods, or embodiments discussed are intended to be only illustrative of the invention disclosed by this specification. Variation of these compositions, methods, or embodiments are readily apparent to a person of skill in the art based upon the teachings of this specification and are therefore intended to be included as part of the inventions disclosed herein.

For example, variations in precipitation methods, such as pH, precipitation agent, aging time, or temperature are considered part of this invention.

For still another example, use of adjuvants before, during, or after alkylation and with or without water to maintain or restore alkylation catalysts such as those disclosed in this invention is contemplated. Reference to halite adjuvants containing bromine, chlorine, or fluorine suitable for this invention are reported in U.S. Pat. No. 3,865,894 (issued Feb. 11, 1975) of Kirsch et al. Other adjuvant additives suitable for this invention are reported in Patent Cooperation Treaty application having international publication W092/04977 and having international application number PCT/US91/06999. $BF_3$ is disclosed to be useful with titanium and zirconium oxides.

For still another variation, the addition of Adamantane, a hydride transfer agent, is useful in this invention. The amount to be added is sufficient to measurably improve yields, this, depending upon temperature, is usually at least (10,000 parts per million in weight, preferably at least 1000 parts per million in weight, and more preferably at least 500 parts per million in weight, as based upon total weight of alkene present.

All percent by weights are based upon the total weight of the calcined catalyst, unless stated otherwise.

Reference made to any other specification is intended to result in such patents or literature being expressly incorporated herein by reference including any patents or other literature references cited within such patents. Any reference to a numerical range is intended to expressly incorporate herein by reference each and every numerical value within such range and each and every numerical range within such range. For example, a given range of 1 to 100 is intent to include 23, a value within the given range of 1 to 100, and 10 to 70, a range within the given range.

What is claimed is:

1. In a method for catalyzing formation of an alkylate from a feed comprising an olefin and a branched alkane, the improvement comprising using as catalyst an acid catalyst comprising a sulfated mixed oxide of titanium and nickel, wherein the percent by weight of titanium is at least 80%; of nickel is in the range 1–4%; and of sulfur in the range 1–10% under appropriate reaction conditions that substantially preclude a temperature treatment of said acid catalyst in excess of about 450° C.

2. The process of claim 1, wherein the branched alkane and olefin are in an average molar ratio of branched alkane to olefin, in the range 1:1 to 1:1000.

3. The process of claim 2, wherein the ratio is in the range 1:1 to 50:1.

4. The process of claim 3, wherein the ratio is in the range 1:1 to 10:1.

5. The process of claim 1, wherein there is additionally an effective concentration of adamantane.

6. The process of claim 5, wherein the effective concentration of adamantane is at least 10,000 parts per million (ppm) by weight, as based on the total weight of olefin.

7. The process of claim 6, wherein the effective concentration of adamantane is at least 1,000 parts per million (ppm) by weight, as based on the total weight of olefin.

8. The process of claim 7, wherein the effective concentration of adamantane is at least 500 parts per million (ppm), by weight as based on the total weight of olefin.

9. In a method for catalyzing reaction of an olefin with a branched alkane, the improvement comprising using as catalyst an acid catalyst comprising a sulfated mixed oxide of titanium and nickel, wherein the percent by weight of titanium is at least 80%; of nickel is in the range 1–4%; and of sulfur in the range 1–10% under appropriate reaction conditions that substantially precludes a reaction temperature in excess of about 450° C.

* * * * *